United States Patent [19]

Simmons

[11] Patent Number: 4,717,386
[45] Date of Patent: Jan. 5, 1988

[54] SAFETY DEVICE FOR A NEEDLE

[76] Inventor: John Simmons, R.D. #2 Independence Ct., Brewster, N.Y. 10509

[21] Appl. No.: 944,436

[22] Filed: Dec. 17, 1986

Related U.S. Application Data

[63] Continuation of Ser. No. 811,499, Dec. 20, 1985, abandoned.

[51] Int. Cl.⁴ ............................................... A61M 5/32
[52] U.S. Cl. ...................................... 604/192; 604/263
[58] Field of Search ........................ 604/192, 263, 187

[56] References Cited

U.S. PATENT DOCUMENTS 4,485,918 12/1984 Mayer ............................. 604/263 X
4,596,562 6/1986 Vernon .................................. 604/263

Primary Examiner—John D. Yasko
Attorney, Agent, or Firm—Rodman & Rodman

[57] ABSTRACT

The safety device for a needle includes a sheath reception opening provided in a cap retainer member or provided in a hand shield portion of the device. The cap retainer member in one embodiment is joined to the hand shield section and in another embodiment is secured to a pair of legs joined at right angles. In another embodiment the cap retainer member is used by itself with an adhesive provided on a base surface thereof. A manually engageable gripping portion is provided at the base surface of the hand shield portion in another embodiment, with a handle extending from the gripping portion beyond the periphery of the hand shield portion. In a further embodiment the handle extends from the hand shield portion. In another embodiment a plurality of cap retainer members are joined to the hand shield portion. In still another embodiment a sheath holding opening is provided in the handle portion. Some embodiments of the safety device can be handheld and used on a support surface. Other embodiments can be used only on a support surface. All embodiments permit the hand which normally holds the protective sheath of a syringe to be isolated from a zone of high risk. Embodiments of the device that are secured to a support surface can be operated with one hand. Use of the handle to stablize the device on a support surface further isolates the hand from the zone of high risk.

33 Claims, 13 Drawing Figures

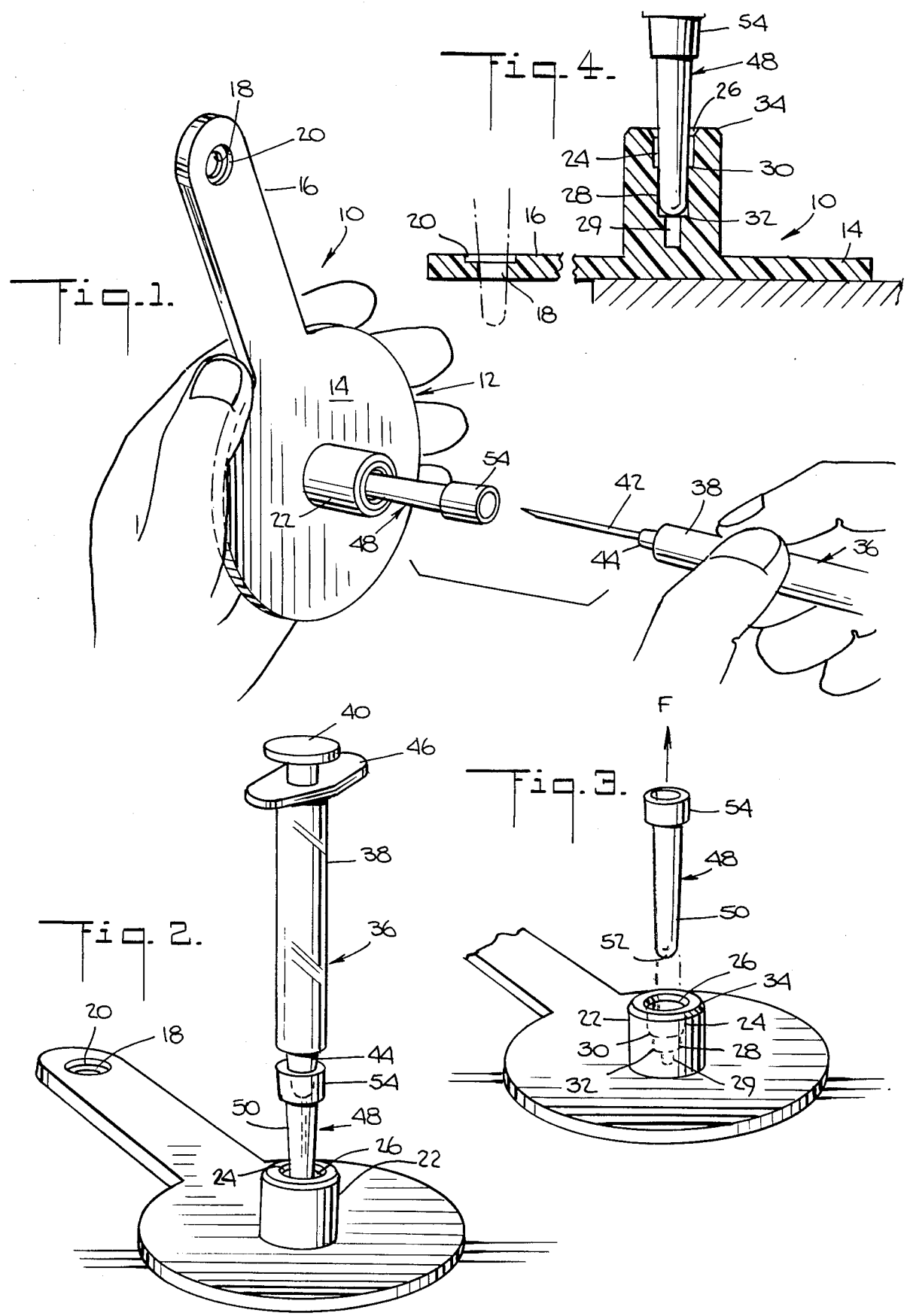

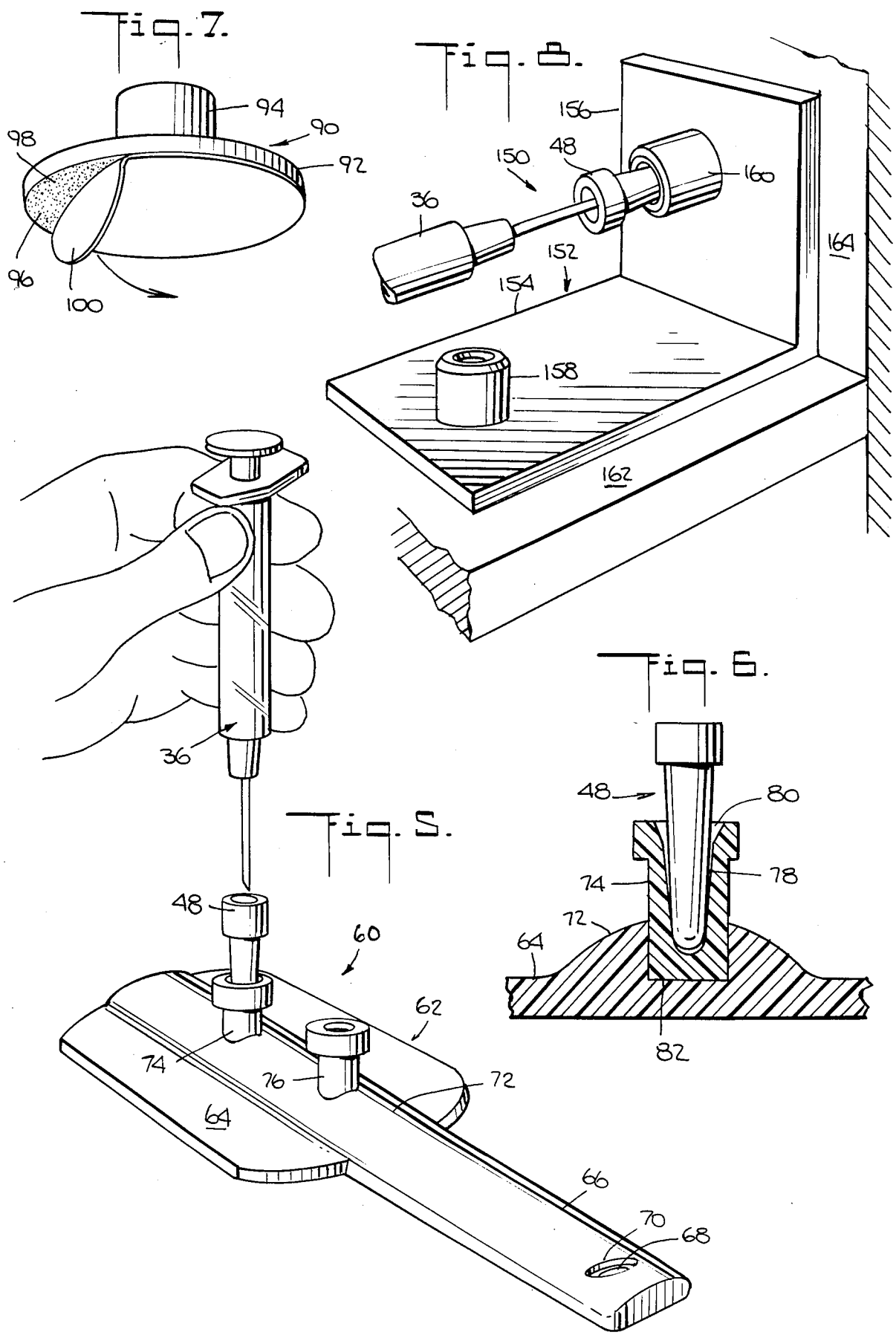

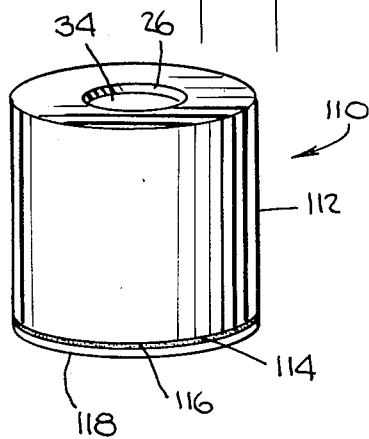
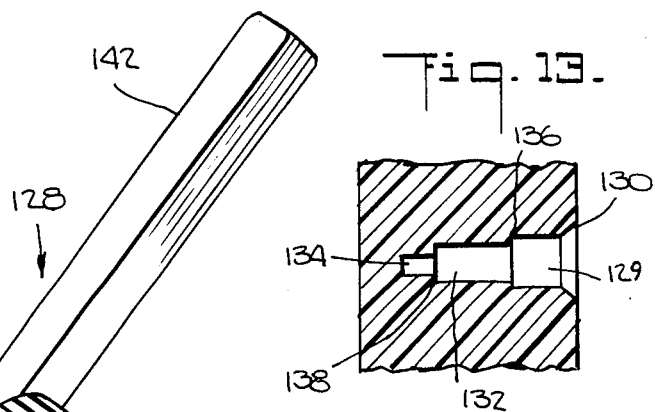
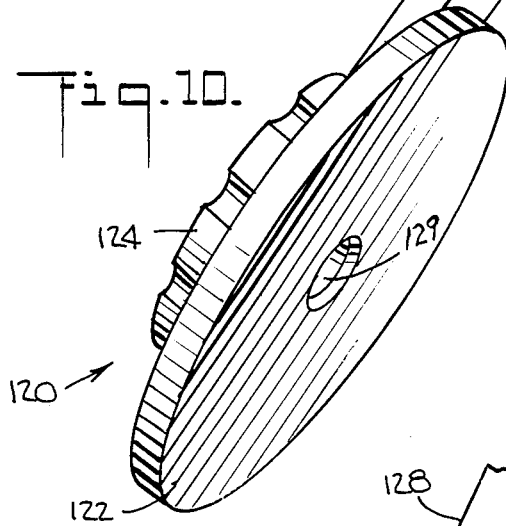
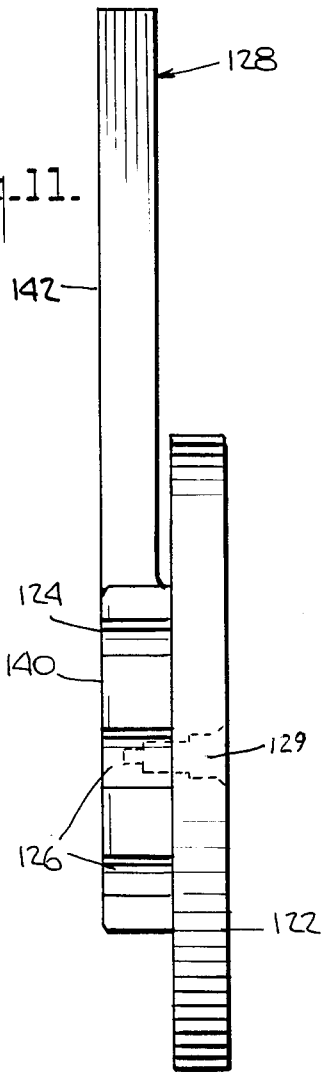
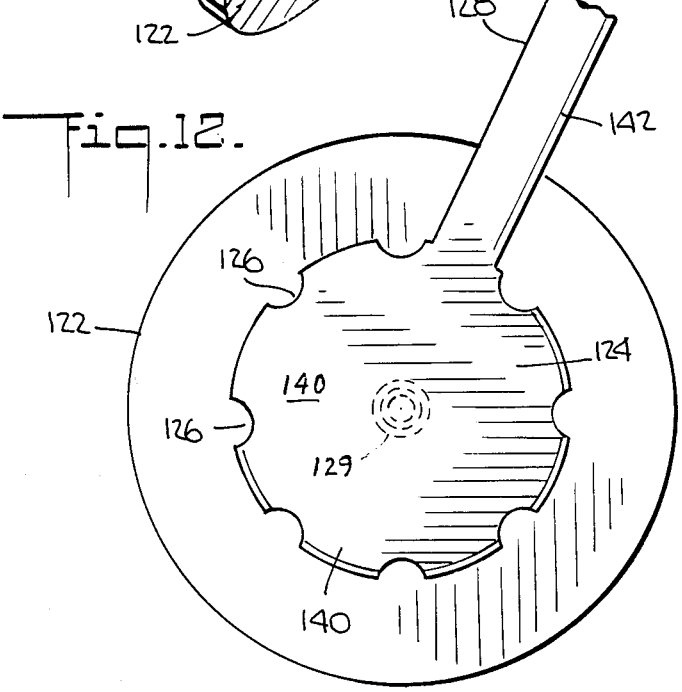

SAFETY DEVICE FOR A NEEDLE

This is a continuation of application Ser. No. 811,499, filed Dec. 20, 1985 now abandoned.

BACKGROUND OF THE INVENTION

This invention relates to safety accessories for medical instruments and more particularly to a safety device for uncapping and recapping the protective sheath of a hypodermic needle.

A typical hypodermic needle or syringe has a hollow needle at one end of a cylindrical fluid container and a moveable plunger at the opposite end of the container. The plunger is used to discharge fluid from the cylinder through the needle, or to draw fluid through the needle into the cylinder.

Ideally, the syringe needle should have a relatively painless entry into the skin. Therefore it is desirable that the needle have the smallest possible cross section and that the tip of the needle be extremely sharp.

Manufacturers of syringe needles in current use have been reasonably successful in producing a needle having the desired size and tip sharpness. However, use of the syringe requires great care since even the most casual contact of the needle with the skin is likely to penetrate the skin, a circumstance commonly known as a needle stick. The term "needle stick", as used herein, refers to an unintended or accidental penetration of the skin by a hypodermic needle.

Although a needle stick is a minor injury, it carries the threat of transmitting such dangerous diseases as hepatitis and AIDS. Furthermore, potentially lethal drugs or toxins can also be accidently transmitted by a needle stick.

Due to the sharpness and delicate structure of the syringe needle, a removable protective sheath or cap, usually made of plastic, is installed over the needle. The protective sheath is an elongated sleeve, slightly longer than the needle. The sheath is closed at one end and has an opposite open end that press-fits onto the base of the needle support structure. The sheath is relatively narrow and protects the needle while permitting safe handling of the syringe when the syringe is not in use.

Before using the syringe, the protective sheath must be removed from the needle, a procedure known as uncapping. During uncapping, the sheath is normally gripped between the fingers of one hand, while the other hand holds the cylinder or main body portion of the syringe. The hand which holds the sheath is usually at greater risk in receiving a needle stick than the hand which holds the syringe. Any contact between the needle tip and the hand during the uncapping process can cause a needle stick.

After the syringe has been used, the protective sheath is often replaced over the needle, a procedure known as recapping. During recapping, the protective sheath is again held in one hand and the main body of the syringe is held in the other hand. The recapping of the sheath onto the needle is accomplished in a manner similar to the replacement of a pen cover onto a pen.

Unfortunately, any distraction, any shake of the hand, and any misalignment of the needle and sheath during recapping is likely to result in a needle stick to the hand which holds the sheath. A high risk zone around the sheath is defined as the immediate area or space surrounding the sheath where a syringe needle will pass if it is misaligned with the sheath. The hand which holds the sheath, especially the fingers are thus located in the high risk zone. Therefore the problem of needle sticks during recapping is endemic to the recapping procedure.

Anyone who has misaligned the cover of a pen with the body of a pen and contacted the hand holding the pen cover with the pen point can appreciate the likelihood of suffering a needle stick. Furthermore, uncapping and recapping the protective sheath of a syringe needle are occasions when needle sticks occur most often.

It is well known that needle sticks to the hands are the most prevalent work site accident in hospitals, physicians' offices and medical laboratories. In view of the dangerous ramifications of needle sticks it is desirable to provide a safety device for use in uncapping and recapping the protective sheath of a syringe without risk of needle sticks to the hands.

OBJECTS AND SUMMARY OF THE INVENTION

Among the several objects of the invention may be noted the provision of a novel safety accessory for a syringe, a novel safety device for a syringe that eliminates the risk of needle sticks to the hands during uncapping and recapping of the protective sheath, a novel safety device for a syringe that grips and holds the protective sheath during uncapping and recapping of a hypodermic syringe needle, a novel safety device for a syringe which grips and holds the protective sheath with a greater force than the detent which holds the sheath on the syringe, and a novel safety device for a syringe which permits isolation of the hand that ordinarily holds the protective sheath, from the high risk zone of the protective sheath during uncapping and recapping.

Other objects and features will be in part apparent and in part pointed out hereinafter.

In accordance with the present invention, the safety device for a syringe includes means for holding the sheath with a predetermined detent during uncapping and recapping of the protective sheath of a hypodermic needle.

The sheath holding means include an opening for accommodating the sheath and engaging means in the opening to hold the sheath with the predetermined detent when the sheath is located in a predetermined position in the opening. The safety device also includes means that permit stablization of the sheath holding means during the uncapping and recapping procedures.

In one embodiment of the invention, the sheath holding means includes a cap retainer member that contains the sheath accommodating opening. In another embodiment of the invention, the sheath holding means include a hand shield member that contains the opening for accommodating the sheath.

In a further embodiment of the invention, the cap retainer member is joined to a hand shield member.

The means for stablizing the sheath holding means during uncapping and recapping include a handle that extends from the hand shield member. In another embodiment the handle can extend from a hand gripping portion that is joined to the hand shield member.

The sheath holding means can also be provided as an opening in the handle.

Stablization of the sheath holding means is also accomplished by providing an adhesive on a base surface of a cap retainer member for bonding the cap retainer member to a support surface. The adhesive can also be provided on a base surface of the hand shield.

In a further embodiment of the invention, two leg portions are joined at right angles to each other and each of the leg portions includes a cap retainer member. Adhesive can be provided on the base surfaces of the leg portions.

In many of the embodiments the uncapping and recapping procedure can be accomplished using one hand only. In other embodiments the safety device can be hand held, necessitating the use of two hands. However, whether one or two hands is employed to carry out the uncapping and recapping operations, the safety device enables the hand which ordinarily holds the sheath to be isolated from the zone of high risk. This isolation is accomplished by fashioning the periphery of the hand shield member to a size that protects the palm of the hand when the hand shield member is held, and also spaces the fingers sufficiently distant from the cap securing opening so as to be outside the zone of high risk.

A hand gripping portion can also be provided at the base of the hand shield portion and having a smaller periphery than the hand shield portion. The safety device is thus held at the hand gripping portion permitting location of the gripping hand behind the hand shield portion during uncapping and recapping. Consequently, there is little or no danger of needle sticks to the hand.

The safety device in another embodiment includes more than one cap retainer member.

In using the safety device for uncapping, the sheath end of the syringe is pushed into the sheath holding opening of the safety device and detented therein. The syringe can then be withdrawn free of the protective sheath for use on a patient. The protective sheath is maintained in a detented position in the safety device while the syringe is being used.

Recapping of the syringe is accomplished by either holding the safety device or stablizing the safety device on a support surface and aligning the needle of the syringe with the protective sheath. Whether the safety device is hand held or disposed on a support surface, the hand which ordinarily holds the sheath is outside the zone of high risk. Therefore, the recapping procedure can be accomplished without the danger of needle sticks to the hand.

The recapped syringe is removed from the safety device by grasping the syringe around the sheath and pulling away from the cap retainer with a force that overcomes the detent force of the safety device on the sheath.

The invention accordingly comprises the constructions hereinafter described, the scope of the invention being indicated in the claims.

DESCRIPTION OF THE DRAWINGS

In the accompanying drawings, in which several embodiments of the invention are illustrated, FIG. 1 is a perspective view of one embodiment of the invention, showing the relationship between the protective sheath and the needle after uncapping and/or just before recapping of a syringe;

FIG. 2 is a perspective view thereof showing the relative position of the syringe after recapping and/or just before uncapping;

FIG. 3 shows the protective sheath separated from the safety device;

FIG. 4 is a side view, partly in section, showing the protective sheath accommodated in the safety device;

FIG. 5 is a perspective view of a further embodiment of the invention;

FIG. 6 is a side view, partly shown in section, of the embodiment of FIG. 5;

FIG. 7 is a perspective view of another embodiment of the invention;

FIG. 8 is a perspective view of still another embodiment of the invention;

FIG. 9 is a perspective view of a further embodiment of the invention;

FIG. 10 is a perspective view of still another embodiment of the invention;

FIG. 11 is a side view thereof;

FIG. 12 is a plan view thereof; and

FIG. 13 is an enlarged fragmentary sectioned view of the sheath holding opening thereof.

Corresponding reference characters indicate corresponding parts throughout the several views of the drawings.

DETAILED DESCRIPTION OF THE INVENTION

A safety device for a syringe, incorporating one embodiment of the invention, is generally indicated by the reference number 10 in FIG. 1.

The device 10 comprises a paddle-shaped member 12 that includes a hand shield section 14. A handle 16, which extends from the hand shield section 14, is formed with a recess 18 having a counterbore 20.

A sheath or cap retainer 22 is formed or otherwise provided at a central portion of the hand shield section 14. As seen most clearly in FIG. 4, the cap retainer 22 includes a recess 24 having a countersink 26, a reduced mid-portion 28 and a reduced end portion 29, thus providing stepped edges at 30 and 32. The cap retainer 22 is chamfered or finished as indicated at 34.

Referring to FIGS. 2 and 3, a conventional syringe, generally indicated at 36, includes a cylindrical container or body 38 having a moveable plunger 40 at one end of the cylinder 38 and a hollow needle 42 at an opposite end. The needle 42 is supported in a tapered needle mount 44 secured to the cylinder 38. A flange 46 on the cylinder can be gripped by the fingers during movement of the plunger 40.

A protective sheath or cap 48, usually formed of plastic, comprises an elongated slightly tapered sleeve 50 having a closed end 52 and an open-ended collar portion 54. The sheath 48 covers the needle 42 when the collar portion 54 is detachably press fitted onto the needle mount 44.

During use of the syringe 36, the protective sheath 48 must be removed or uncapped from the needle 42. After the syringe has been used, the needle 42 should be recapped with the protective sheath 48. Under conventional practice, both the uncapping and recapping procedures are usually accomplished by holding the syringe 36 in one hand and gripping the protective sheath 48 between the fingers of the other hand, also referred to as the sheath gripping hand. Through a coordinated movement of both hands, the sheath 48 is either removed or replaced back onto the needle 42 in much the same fashion as a pen cover (not shown) is removed from and/or replaced onto a pen body (not shown).

Any misalignment of the needle 42 and the sheath 48 during uncapping and recapping may result in a needle stick to the hand which holds the sheath 48. Especially vulnerable to needle sticks are the fingers which directly grip the periphery of the sheath 48, and the exposed palm of the hand which holds the sheath 48. The spac around the sheath 48 that is occupied by the fingers which grip the sheath 48, and the exposed palm of the hand which holds the sheath 48 define a zone of high risk. The high risk zone represents the general area that the needle 42 will usually enter if it is misaligned with the sheath 48 especially during the recapping procedure.

The safety device 10 performs the gripping function ordinarily performed by the hand that controls the protective sheath 48. The safety device 10 thus permits the sheath gripping hand to be isolated from the zone of high risk thereby eliminating the likelihood of needle sticks during the uncapping and recapping procedures.

In using the safety device 10 for uncapping, the paddle-shaped member 12 can be placed on a countertop or any suitable support surface. The sheathed end of the syringe 36 is directed into the recess 24 of the cap retainer 22 as shown in FIG. 2. Downward pressure is exerted on the syringe 36 to cause the stepped edges 30 and 32 of the recess 24 to engage against the tapered periphery of the sheath 48. The stepped edges 30 and 32 thus detent and hold the sheath 48 with a greater force than the detent provided by the press fit between the collar portion 54 and the needle mount 44.

Referring to FIG. 2, the syringe 36 is then withdrawn from the protective sheath 48, which is detented in the cap retainer 22. The hand which ordinarily holds the protective sheath 48 can be used to steady the handle 16 to stabilize the safety device 10 during uncapping. The sheath gripping hand is thus located outside the high risk zone that surrounds the sheath 48.

The safety device 10 essentially performs the function of the sheath gripping hand by gripping and holding the sheath 48 during uncapping. Although the sheath 48 is gripped by the cap retainer 22 during uncapping, said sheath can be separated from the retainer 22 with a slight upward force F as shown in FIG. 3.

In using the safety device 10 for recapping, the syringe needle 42 is aligned with the sheath 48 in the manner shown in FIG. 6, although the embodiment under discussion is that of FIG. 2. The needle end of the syringe is inserted into the sheath 48 which is held in an upright position by the safety device 10 as shown in FIG. 4. The hand which would ordinarily hold the sheath 48 is not needed to accomplish the recapping procedure and can thus be kept away from the high risk zone.

Should the needle 42 misalign with the protective sheath 48 during uncapping, and pass alongside the protective sheath 48, or the cap retainer 22, there is no danger of needle sticks because the protective sheath 48 is gripped not by the fingers, but by the safety device 10. Since the safety device 10 permits the sheath gripping hand to be removed from the zone of high risk during the recapping procedure, the danger of needle sticks is eliminated.

After the recapping has been completed, the sheathed syringe can be removed from the cap retainer 22 by holding both the syringe body 38 and the protective sheath 48 in one hand and pulling away from the cap retainer 22. Since the needle 42 is covered by the protective sheath 48, there is no danger of needle sticks during this removal procedure.

If desired, the safety device 10 can be hand-held during the uncapping or recapping procedures as shown in FIG. 1. For example, during uncapping, the hand shield section 14 can be gripped in one hand while the syringe 36 is held in the other hand. The sheathed end of the syringe is aligned with the recess 24 of the cap retainer 22. The sheath 48 is then pressed into the recess 24 for detachable securement by the cap retainer 22. Since the hand shield section 14 of the safety device 10 is of a predetermined size that covers a substantial portion of the sheath gripping hand, and permits isolation of said hand from the zone of high risk, the likelihood of needle sticks to the fingers or palm of the sheath gripping hand during uncapping is remote.

During recapping, the safety device 10 is likewise held in one hand in the manner shown in FIG. 1. The other hand, holding the syringe 36, directs the needle 42 into the protective sheath 48 which is maintained in position by the cap retainer 22.

If, during the recapping process, the needle 42 is misaligned with the sheath 48 there is no danger of needle sticks to the fingers because they are isolated from the sheath 48 by the hand shield 14. Furthermore, even if needle movement continues toward the palm of the hand, the needle 42 will bottom against the hand shield 14 which shields and protects the hand.

Thus, whether the safety device 10 is used on a support surface or is hand-held, it helps eliminate the risk of needle sticks during the uncapping and recapping procedures.

The recess 18 in the handle 16 is generally used to hang the device 10 on a hook (not shown) when the device 10 is not in use. However, the recess 18 has also been designed to accommodate a sheath of a different size than is accommodated in the cap retainer 22.

For example, since hypodermic needles vary in size and shape, a predetermined size range of protective sheaths can be accommodated in the cap retainer 22. Sheaths which are larger than size range accommodated by the cap retainer 22 can be accommodated in the recess 18 in the manner shown dotted in FIG. 4. The recess 18 and the counterbore 20 are of a predetermined size to accommodate a predtermined size range of such sheaths. This accommodation is accomplished by virtue of engagement between the outer peripheral surface of the sheath with the inner peripheral surface of the recess 18. Since the sheath generally has a slight taper and the recess 18 is open, sheaths of different size can be accommodated to the extent that they would fit inside the recess 18.

A sheath of relatively narrow diameter would project a greater amount below the recess 18 than a sheath of relatively large diameter. Thus, during use of the recess 18 for sheath retention purposes, the cap retainer 22 must be empty and the handle portion 16 should be cantilevered over the edge of a support surface.

If desired, the recess 18 can also be used for uncapping and recapping while the device 10 is hand-held, as shown in FIG. 1. However, the sheath gripping hand must grip the hand shield portion 14 rather than the handle 16 to sufficiently isolate said hand from the high risk zone.

Another embodiment of the safety device is generally indicated by the reference number 60 in FIG. 5. The device 60 comprises a paddle-shaped member 62 that includes a hand shield section 64. A handle 66 which extends from the hand shield section 64 is formed with a recess 68 having a counterbore 70.

The hand shield section 64 includes a median bulge 72 that is a continuation of the contour of the handle 66. A pair of cap retainer members 74 and 76 can be removably threaded, adhered or otherwise affixed to the median bulge 72. The cap retainer 74 includes a tapered recess 78 and a countersink 80. The recess 78 is sized to engage in press-fitting relationship with the protective sheath 48 of the syringe 36.

The cap retainer 76 can be identical to the cap retainer 74 or, if desired, can be sized to accommodate a protective sheath that is of a different size from the sheath 48. Since the cap retainer 74 will accommodate a predetermined size range of sheaths, the cap retainer 76 can be structured to accommodate a different size range of sheaths.

The device 60 can be used on a support surface in a manner similar to that previously described for the device 10. The device 60 can also be used in hand-held fashion in the manner previously described for the device 10. It should be noted that the cap retainers 74 and 76 are located on the hand shield section 64 at positions that ensure that the hand which holds the device 60 is sufficiently isolated from the zone of high risk.

The recess 68 and the counterbore 70 in the handle 66 are identical to the recess 18 and the counterbore 20 of the device 10, and can be used as a hanger or as a further sheath accommodating means in the manner previously described for the device 10.

A further embodiment of the safety device is generally indicated by the reference number 90 in FIG. 7. The device 90 comprises a disc shaped member 92. The member 92 includes a centrally located cap retainer 94 identical to the cap retainer 22. An adhesive coating 96 is provided on an undersurface 98 of the hand shield 92, and a peel off cover sheet 100 covers and protects the integrity of the adhesive coating 96 until the device 90 is ready for use.

In using the device 90, the cover sheet 100 is peeled away and the undersurface 98 is positioned on a clean, dry support surface that is compatible with the adhesive coating 96. The adhesive 96 can be selected to provide a permanent or detachable bond to the support surface. If the bond is detachable, the adhesion should be sufficient to stabilize the member 92 in the support surface during uncapping and recapping, which are carried out in a manner similar to that previously described for the device 10.

The disc-shaped member 92 of the device 90 can be sized to permit hand-held use. However, hand-held use of the device 90 would require that the diameter of the disc shaped member 92 be sufficiently large to function as a hand shield. The member 92 must be of a predetermined size that insures that the fingers and palm of the hand which holds the device 90 are outside the zone of high risk. If handheld use is desired, the cover sheet 100 would remain in place over the adhesive 96. If handheld use is to be the primary method of uncapping and recapping, the adhesive 96 and the cove sheet 100 can be omitted.

Another embodiment of the safety device is generally indicated by the reference number 110 in FIG. 9. The device 110 comprises a cap retainer member 112, substantially identical to the cap retainer 22 of the device 10. The cap retainer 112 includes a base surface 114 having an adhesive coating 116 protected by a cover sheet 118.

In using the device 110 the cover sheet 118 is removed to expose the adhesive 116, and the cap retainer 112 is adhered to any suitable support surface. The uncapping and recapping procedures are then carried out in a manner similar to that previously described for the device 10. It should be noted that the device 110 is not intended for hand-held use unless the diameter of the cap retainer member 112 is made large enough to isolate the fingers and palm of the hand from the zone of high risk.

A further embodiment of the invention is generally indicated by the reference number 120 in FIG. 10. The device 120 comprises a hand shield member 122 joined to a knob 124 that is of smaller diameter than the hand shield member 122. The knob 124 includes a plurality of peripheral cut out portions 126 to facilitate handling of the knob 124. A handle member 128 extends from the knob 124 beyond the periphery of the hand shield member 122. The device 120 also includes a recess 129 having a countersink 130, a reduced mid-portion 132 and a reduced end portion 134, thus providing stepped edges at 136 and 138.

The device 120 can be used in a manner similar to that described for the device 10. For example, the device 120 can be placed on a support surface since the knob 124 has a flat base surface 140 which is continuous and coplanar with the surface 142 of the handle 128. With the device 120 thus supported, the uncapping and recapping procedures are carried out in a manner similar to that described for the device 10.

The device 120 can also be hand held whereby the fingers of the hand engage around the periphery of the knob 124. The cut out portions 126 facilitate holding of the knob 124. If desired, knurls or other surface embossments can be provided to facilitate handling of the knob 124.

Since the hand shield member 122 extends beyond the periphery of the knob 124, the hand shield member 122 forms a protective barrier for the hand during the uncapping and recapping procedures. The uncapping and recapping procedures, when using the device 120 in hand-held fashion, are carried out in a manner previously described for the device 10. It should be noted that the hand shield member 122 is of a predetermined diameter to provide an effective shield that protects the hand during any misalignment between the needle 42 and the sheath 48 which results in the needle bypassing the sheath and moving toward the hand which holds the device 120. The risk of needle sticks to the hand is thus substantially eliminated.

Still another embodiment of the safety device is generally indicated by the reference number 150 in FIG. 8. The device 150 comprises an angle piece 152 having a pair of legs 154 and 156 joined at a substantially right angle. The legs 154 and 156 respectively include cap retainers 158 and 160, identical to the cap retainer 22. The cap retainers 158 and 160 are either formed integrally with the angle piece 152 or are separately attached to the legs 154 and 156 by adhesion or other form of affixation.

Preferably, the safety device 150 is supported on a countertop 162 with a back piece or wall 164. Although not necessary, an adhesive or fastener (not shown) can secure the device 150 to the countertop 162 or to the wall 164. If desired, the device 150 can be used without affixation to the countertop 162 or the back wall 164.

In using the device 150, a choice is made as to which of the cap retainer members 158 or 160 is to be used. If it is desired to use the cap retainer 160 for uncapping and recapping, then the hand which ordinarily grips the sheath 48 can be used to steady the leg 154, assuming there is no affixation of the device 150. The steadying hand is thus away from the high risk zone of the cap retainer 160. The uncapping and recapping of the syringe 36 is then accomplished in a manner similar to that previously described for the device 10.

If it is desired to use the cap retainer 158 for uncapping and recapping, then the hand which ordinarily grips the sheath 48 can be used to steady the leg 156. The steadying hand is thus away from the high risk zone of the cap retainer 158.

If the device 150 is adhered or affixed to the countertop 162 and/or the back wall 164, the uncapping and recapping becomes a one handed operation. Thus, the hand which holds the syringe 36 locates the sheath 48 in the cap retainer 158 or 160 for uncapping. Recapping is accomplished by using the same hand to hold the syringe 36 and align the needle 42 with the sheath 48 that has been previously retained by either the cap retainer 158 or the cap retainer 160. The hand which ordinarily would hold the sheath 48 is thus not needed for uncapping or recapping, thereby eliminating the danger of needle sticks to the hand.

The safety devices 10, 60, 90, 110, 120 and 150 can be formed of a suitable metal or plastic, or an assembly of both materials. The stepped recess 24 of the safety device 10 can be substituted for the tapered recess 78 of the safety device 60. Similarly, the tapered recess 78 of the safety device 60 can be substituted for the stepped recess 24 of the safety device 10.

As will be apparent to those skilled in the art, devices for drawing fluids such as blood also include needles which require capping and uncapping in a manner similar to that described for the syringe 36. Accordingly, the principles and concepts of this invention contemplate adaptation to such fluid drawing devices of the type sold under the trademark Vacutainer manufactured by Vacutainer Systems of Rutherford, N.J.

It will also be apparent that devices such as sharps used for cutting or puncturing purposes, including scalpels and finger puncture devices such as Hemolets, can be accommodated in the safety device until they are brought to a disposal area. Thus, the disclosed safety device is adaptable to puncturing devices that include needles and sharps.

Some advantages of the present invention evident from the foregoing description include a safety device which permits a hand that is normally vulnerable to needle sticks to be positioned outside a zone of high risk, thereby substantially eliminating the danger of needle sticks to the hand. Some embodiments of the invention such as the embodiments of FIGS. 7, 8 and 9 permit the uncapping and recapping process to be accomplished with use of only one hand. All embodiments of the invention which permit isolation of the hand from the zone of high risk or total elimination of one of the hands from the uncapping and recapping operation have thus responded to the critical problem of needle sticks and have solved the problem by rendering the uncapping and recapping procedures substantially risk free with regard to the hazard of needle sticks.

In view of the above, it will be seen that the several objects of the invention are achieved and other advantageous results attained.

As various changes can be made in the above construction without departing from the scope of the invention, it is intended that all matter contained in the above description or shown in the accompanying drawings shall be interpreted as illustrative and not in a limiting sense.

What is claimed is:

1. A device for uncapping and recapping a removable protective sheath of a needle comprising, a plate-like member having one surface provided with at least one sheath holding means and an opposite flat planar surface, said sheath holding means including a sheath retainer with a reces for accommodating said sheath, engaging means in said sheath retainer for detenting said sheath in said recess with a predetermined detent when said sheath is located in a predetermined position in said recess, said sheath retainer having a closed end portion to prevent projection of the detented sheath beyond said opposite flat planar surface whereby the opposite flat planar surface can make surface-to-surface contact with a flat support surface thereby permitting stable positioning of said plate-like member on the flat surface when said sheath is disposed in said recess.

2. The device as claimed in claim 1 including two sheath holding means.

3. The device as claimed in claim 1 wherein said sheath retainer and said plate-like member are formed together.

4. The device as claimed in claim 1 wherein said sheath retainer is formed separately from said plate-like member and joined to said plate-like member.

5. The device as claimed in claim 4 wherein said sheath retainer has a base surface and said means to an adhesive provided on said base surface.

6. The device as claimed in claim 1 further including an adhesive provided on said opposite flat planar surface.

7. The device as claimed in claim 1 wherein said plate-like member includes a leg member.

8. The device as claimed in claim 7 including a pair of said leg members joined at right angles, said sheath holding means including a cap retainer member joined to each of said respective leg members.

9. The device as claimed in claim 1 wherein said said sheath retainer is provided in said plate-like member.

10. The device as claimed in claim 9 wherein the plate-like member has a first predetermined periphery, said device further including a gripping portion joined to said plate-like member and wherein said gripping portion is of lesser peripheral dimension than the plate-like member.

11. The device as claimed in claim 10 wherein a handle member extends from the periphery of said gripping portion beyond the periphery of said plate-like member.

12. The device as claimed in claim 1 wherein a handle member extends from said plate-like member.

13. The device as claimed in claim 12 wherein said handle member is co-planar with said oppposite flat planar surface.

14. The device as claimed in claim 12 wherein said plate-like member and said handle member are paddle-shaped 15. The device as claimed in claim 12 including two sheath holding means projecting from said one surface.

16. The device as claimed in claim 15 wherein said two sheath holding means are coliner with said handle.

17. The device as claimed in claim 15 wherein the respective recesses of said two sheath holding means are identical.

18. The device as claimed in claim 17 wherein the respective recesses of said two sheath holding means are of different size to accommodate different size ranges of sheaths.

19. The device as claimed in claim 1 wherein said plate-like member has a predetermined peripheral extent to permit holding of said plate-like member such that when said plate-like member is held in the hand, said plate-like member shields the palm of the hand.

20. The device as claimed in claim 1 wherein said engaging means in said recess is formed to hold said sheath with a first predetermined detent force greater than the holding force between said sheath and said needle, to permit retention of said sheath in said sheath holding means when said sheathed needle is pulled away from said sheath holding means.

21. The device as claimed in claim 1 wherein said sheath retainer projects from said plate-like member.

22. The device as claimed in claim 1 wherein said recess is tapered and said engaging means include the tapered surface of said recess.

23. The device as claimed in claim 1 wherein said recess is stepped and said engaging means include the stepped edges of said recess.

24. The device as claimed in claim 7, wherein said leg member is joined at a right angle to said plate-like member and a second said sheath retainer is joined to said leg member.

25. the device as claimed in claim 1, including a plurality of said sheath retainers.

26. The device a claimed in claim 1, wherein the plate-like member has a first predetermined periphery, said device further including a gripping portion joined to said plate-like member and wherein said gripping portion is of lesser peripheral dimension than the plate-like member.

27. The device as claimed in claim 1, wherein said sheath retainer includes a blind recess in said plate-like member.

28. The device as claimed in claim 27, wherein said plate-like member has a periphery that extends a predetermined amount beyond the recess of said sheath retainer portion to permit holding of said plate-like member whereby the plate-like member shields the palm of the hand and permits protective positioning of the fingers of the hand away from said recess when said plate-like member is held in the hand.

29. The device as claimed in claim 27, including two sheath retainers in said plate-like member.

30. A device for uncapping and recapping a removeable protective sheth of a needle comprising, a plate-like hand shield member having one surface provided with at least one sheath retainer portion and an opposite flat planar surface which can make surface to surface contact with a flat support surface, said sheath retainer portion projecting from said one surface and including a blind recess for accommodating and holding said sheath with a predetermined detent when said sheath is located in a predetermined position in said recess, to permit the needle to be pulled away from the detented sheath, said plate-like member having a periphery that extends a predetermined amount beyond the projecting sheath retainer portion to permit holding of said plate-like member and to shield the palm of the hand and permit protective positioning of the fingers of the hand away from said projecting sheath retainer portion when said plate-like member is held in the hand.

31. The device as claimed in claim 30, including two said sheath retainer portions projecting from said one surface.

32. A device for uncapping and recapping the protective sheath of a needle comprising a hand shield portion including an opening therein for accommodating and holding said sheath with a predetermined detent when said sheath is located in a predetermined position in said opening, and a manually engageable gripping portion joined to said hand shield portion, said hand shield portion having a first predetermined periphery and said manually engageable gripping portion having a periphery of lesser dimension than said hand shield portion.

33. A device for uncapping and recapping the protective sheath of a needle comprising a cap retainer member including an opening therein for accommodating and holding said sheath with a predetermined detent when said sheath is located in a predetermined position in said opening, said cap retainer member having a base surface and an adhesive provided on said base surface for securing said cap retainer to a support surface.

* * * * *

UNITED STATES PATENT AND TRADEMARK OFFICE
CERTIFICATE OF CORRECTION

PATENT NO. :  4,717,386

DATED      :  January 5, 1988

INVENTOR(S) :  John Simmons

It is certified that error appears in the above-identified patent and that said Letters Patent is hereby corrected as shown below:

```
At column 5,
     line 2, change "spac" to --space--.

At column 7,
     line 54, change "cove" to --cover--.

At column 10,
     line 6, change "reces" to --recess--;
     line 26, delete "said means to";
     line 59, change "coliner" to --colinear--.

At column 12,
     line 4, change "sheth" to --sheath--.
```

Signed and Sealed this

Ninth Day of August, 1988

Attest:

DONALD J. QUIGG

Attesting Officer

Commissioner of Patents and Trademarks